United States Patent
Otomaru et al.

(10) Patent No.: US 7,279,537 B2
(45) Date of Patent: Oct. 9, 2007

(54) TRANSITION METAL COMPLEXES AND POLYMERIZATION CATALYSTS

(75) Inventors: Yuka Otomaru, Kyoto (JP); Hidenori Hanaoka, Suita (JP); Takayuki Higashii, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/532,048

(22) PCT Filed: Oct. 15, 2003

(86) PCT No.: PCT/JP03/13169

§ 371 (c)(1),
(2), (4) Date: Jan. 31, 2006

(87) PCT Pub. No.: WO2004/037835

PCT Pub. Date: May 6, 2004

(65) Prior Publication Data

US 2006/0229195 A1 Oct. 12, 2006

(30) Foreign Application Priority Data

Oct. 23, 2002 (JP) ............................. 2002-308102

(51) Int. Cl.
 C08F 4/69 (2006.01)
 C07F 11/00 (2006.01)
 C07F 9/50 (2006.01)
(52) U.S. Cl. .................. 526/169; 526/161; 502/103; 502/132; 502/160; 502/171; 556/21; 556/57

(58) Field of Classification Search .................. 556/21, 556/57; 502/171, 103, 104, 132, 140; 526/133, 526/161, 169
See application file for complete search history.

(56) References Cited

U.S. PATENT DOCUMENTS 4,115,318 A 9/1978 Speca
5,585,510 A 12/1996 Mazany

FOREIGN PATENT DOCUMENTS

JP 10-218922 A 8/1998
WO WO-87/02370 A1 4/1987

*Primary Examiner*—Caixia Lu
(74) *Attorney, Agent, or Firm*—Birch, Stewart, Kolasch & Birch, LLP

(57) ABSTRACT

There are provided a transition metal complex of formula (1):

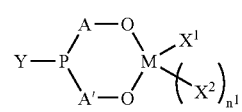

(1)

wherein M represents an element of Group 6 of Periodic Table of Elements, A and A' are the same or different, and represent a substituted or unsubstituted C1-10 alkylene group or the like, Y represents a substituted or unsubstituted C1-10 alkyl group, or the like, $X^1$ and $X^2$ are the same or different, and represent a hydrogen atom, a halogen atom, a substituted or unsubstituted C1-10 alkyl group, or an amino group disubstituted with C1-20 hydrocarbon, and $n^1$ is an integer of 0 to 3, an olefin polymerization catalyst obtained by combining a transition metal complex with an organic aluminum or aluminoxane, a polymerization catalyst further containing a boron compound, and a process for producing olefin polymer using the polymerization catalyst.

6 Claims, No Drawings

TRANSITION METAL COMPLEXES AND POLYMERIZATION CATALYSTS

TECHNICAL FIELD

The present invention relates to transition metal complexes, olefin polymerization catalysts and a process for preparing olefin polymers.

Backgroun Technique

WO87/02370 reports that 2,2'-thiobis(6-tert-butyl-4-methylphenoxy)titanium dichloride is used as a component of an olefin polymerization catalyst, and JP-A No. 10-218922 reports that 2,2'-(phenylphosphido)bis(6-tert-butyl-4-methylphenoxy)(tetrahydrofuran)titanium dichloride is used as a component of an olefin polymerization catalyst. However, these catalysts are not industrially necessarily satisfactory in their activity.

DISCLOSURE OF THE INVENTION

According to the present invention, an olefin polymerization catalyst having better activity is obtained from a novel transition metal complex, and olefin polymers can be industrially advantageously prepared by a method of polymerizing olefin using the catalyst.

That is, the present invention provides
a transition metal complex of formula (1):

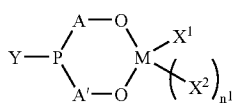

(1)

wherein M represents an element of Group 6 of Periodic Table of Elements,

A and A' are the same or different and represent
a substituted or unsubstituted C1-10 alkylene group,
a substituted or unsubstituted C6-18 phenylene group,
a substituted or unsubstituted C10-20 naphthylene group or
a silylene group substituted with a substituted or unsubstituted C1-20 hydrocarbon, Y represents a substituted or unsubstituted C1-10 alkyl group,
a substituted or unsubstituted C7-20 aralkyl group,
a substituted or unsubstituted C6-20 aryl group or
a silyl group substituted with a substituted or unsubstituted C1-20 hydrocarbon, $X^1$ and $X^2$ are the same or different, and represent
a hydrogen atom, a halogen atom,
a substituted or unsubstituted C1-10 alkyl group,
a substituted or unsubstituted C7-20 aralkyl group,
a substituted or unsubstituted C6-20 aryl group,
a substituted or unsubstituted C1-10 alkoxy group,
a substituted or unsubstituted C7-20 aralkyloxy group,
a substituted or unsubstituted C6-20 aryloxy group, or
an amino group disubstituted with C1-20 hydrocarbon, and $n^1$ is an integer of 0 to 3;

an olefin polymerization catalyst which is obtained by combining the transition metal complex with the following compound (A):

compound (A): any one of the following compounds ($A_1$) to ($A_3$), or a mixture of two or more of them ($A_1$): an organic aluminum compound of formula: $(E_1)_a Al(Z')_{(3-a)}$, ($A_2$): cyclic aluminoxane having a structure of formula: $\{-Al(E_2)-O-\}_b$, ($A_3$): linear aluminoxane having a structure of formula: $(E_3)\{-Al(E_3)-O-\}_c Al(E_3)_2$ wherein $E_1$ to $E_3$ are the same or different, and represent a C1-8 hydrocarbon group, Z's are the same or different and represent a hydrogen atom or a halogen atom, a represent 1, 2 or 3, b represents an integer of 2 or more, and c represent an integer of 1 or more;

an olefin polymerization catalyst which is obtained by combining the aforementioned olefin polymerization catalyst and the following compound (B):

compound (B): any one of the following compounds ($B_1$) to ($B_3$), or a mixture of two or more of them:

($B_1$): a boron compound of formula $BQ_1Q_2Q_3$, ($B_2$): a boron compound of formula $Z^+(BQ_1Q_2Q_3Q_4)^-$, ($B_3$): a boron compound of formula $(L-H)^+ (BQ_1Q_2Q_3Q_4)^-$ wherein B is a trivalent boron atom, $Q_1$ to $Q_4$ are the same or different and represent a halogen atom, a C1-20 hydrocarbon group, a halogenated C1-20 hydrocarbon group, a silyl group substituted with C1-20 hydrocarbon, an C1-20 alkoxy group, or an amino group disubstituted with C1-20 hydrocarbon, $Za^+$ represents an inorganic or organic cation, and L represents a neutral Lewis base;

a process for preparing an olefin polymer utilizing the polymerization catalyst, and a process for preparing a transition metal complex of formula (1), which process comprise reacting a compound of formula (3):

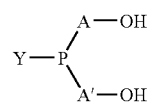

(3)

wherein Y, A and A' are as defined above, with a transition metal compound of formula (4):

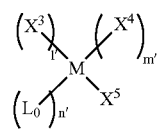

(4)

wherein M represents an element of Group 6 of Periodic Table of Elements, $X^3$, $X^4$ and $X^5$ are the same or different, and represent
a hydrogen atom, a halogen atom,
a substituted or unsubstituted C1-10 alkyl group,
a substituted or unsubstituted C7-20 aralkyl group,
a substituted or unsubstituted C6-20 aryl group,
a substituted or unsubstituted C1-10 alkoxy group,
a substituted or unsubstituted C7-20 aralkyloxy group, a substituted or unsubstituted C6-20 aryloxy group, or an amino group disubstituted with C1-20 hydrocarbon, $L_0$ represents a neutral ligand selected from ether, sulfide, amine, phosphine or olefin, and l', m' and n' represent independently an integer of 0 to 2.

BEST MODE FOR CARRYING OUT THE INVENTION

The present invention will be explained in detail below.

Examples of the substituted or unsubstituted C1-10 alkylene group of formula A or A' in the compound of formula (1) or (3) include, for example, a group of formula:

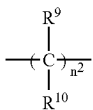

wherein $R^9$ and $R^{10}$ represent the substituents as defined below and $n^2$ is an integer of 1 to 10.

Examples of the substituted or unsubstituted C6-18 phenylene group represented by A or A' in the compound of formula (1) or (3) include a group of formula:

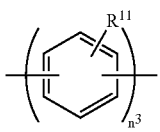

wherein $R^{11}$ is as defined below, and $n^3$ is an integer of 1 to 3.

Examples of the substituted or unsubstituted C10-20 naphthylene group of formula: A or A' in the compound of formula (1) or (3) include, for example, a group of formula:

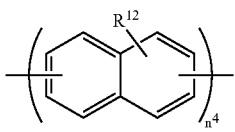

wherein $R^{12}$ represents the substituents as defined below, and $n^4$ is 1 or 2.

Examples of the substituted or unsubstituted silynene group substituted with C1-20 hydrocarbon, represented by A, or A' in the compound of formula (1) or (3) include, for example, a group of formula:

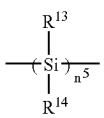

wherein $R^{13}$ and $R^{14}$ are as defined below, and $n^5$ is 1 or 2.

In the aforementioned formulas, $R^9$, $R^{10}$, $R^{11}$, $R^{12}$, $R^{13}$ and $R^{14}$ are the same or different, and represent a hydrogen atom, a halogen atom, a substituted or unsubstituted C1-10 alkyl group, a substituted or unsubstituted C1-10 alkoxy group, or a silyl group substituted with C1-20 hydrocarbon. $n^2$ and $n^3$ are preferably 1 or 2.

Examples of the halogen atom in $R^9$ to $R^{14}$ include a fluorine atom, a chlorine atom, a bromine atom and an iodine atom, and preferred is a chlorine atom.

Examples of the unsubstituted C1-10 alkyl group in $R^9$ to $R^{14}$ include a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group, a n-nonyl group, and a n-decyl group. Examples of the substituted C1-10 alkyl group include an C1-10 alkyl group substituted with a substituent selected from the group consisting of a halogen atom (e.g. a fluorine atom or a chlorine atom etc.), an alkoxy group (e.g. a methoxy group etc.), an aryloxy group (e.g. a phenoxy group etc.), an amino group substituted with hydrocarbon (e.g. a dimethylamino group etc.) and a silyl group substituted with hydrocarbon (e.g. a trimethylsilyl group etc.), and specific examples thereof include a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorodecyl group, a trichloromethyl group, a methoxymethyl group, a phenoxymethyl group, a dimethylaminomethyl group, and a trimethylsilylmethyl group. Among them, a methyl group, an ethyl group, an isopropyl group, a tert-butyl group, and an amyl group are preferred, and a more preferred is a tert-butyl group.

In $R^9$ to $R^{14}$, examples of the unsubstituted C1-10 alkoxy group include a methoxy group, an ethoxy group, a n-propoxy group, an isopropoxy group, a n-butoxy group, a sec-butoxy group, a tert-butoxy group, a n-pentyloxy group, a neopentyloxy group, a n-hexyloxy group, a n-octyloxy group, a n-nonyloxy group, and a n-decyloxy group. Examples of the substituted C1-10 alkoxy group include an C1-10 alkoxy group substituted with a substituent selected from the group consisting of a halogen atom (e.g. a fluorine atom or a chlorine atom etc.), an alkoxy group (e.g. a methoxy group, an ethoxy group etc.), an aryloxy group (e.g. an phenoxy group etc.), an amino group substituted with hydrocarbon (e.g. a dimethylamino group etc.) and a silyl group substituted with hydrocarbon (e.g. a trimethysilyl group etc.). Examples the substituted alkoxy group include, for example, a fluoromethoxy group, a difluoromethoxy group, a trifluoromethoxy group, a fluoroethoxy group, a difluoroethoxy group, a trifluoroethoxy group, a tetrafluoroethoxy group, a pentafluoroethoxy group, a perfluoropropoxy group, a perfluorobutyloxy group, a perfluoropentyloxy group, a perfluorohexyloxy group, a perfluorooctyloxy group, a perfluorodecyloxy group, a trichloromethoxy group, a methoxymethyl group, a phenoxymethoxy group, a dimethylaminomethoxy group, and a trimethylsilylmethoxy group. Preferred alkoxy group are a methoxy group, an ethoxy group and a tert-butoxy group.

In $R^9$ to $R^{14}$, examples of the hydrocarbon group of the silyl group substituted with substituted or unsubstituted C1-20 hydrocarbon include an C1-10 alkyl group such as a methyl group, an ethyl group, a n-propyl group, an isopropyl group, a n-butyl group, a sec-butyl group, a tert-butyl group, a n-pentyl group, a neopentyl group, an amyl group, a n-hexyl group, a cyclohexyl group, a n-octyl group, a n-nonyl group, or a n-decyl group, and an C6-20 aryl group such as a phenyl group, a tolyl group, a xylyl group, a naphtyl group, or an anthracenyl group.

Examples of the silyl group substituted with the C1-20 hydrocarbon include a monosubstitued silyl group such as a methylsilyl group, an ethylsilyl group, and a phenysilyl group, a disubstitued silyl group such as a dimethylsilyl group, a diethylsilyl group, a diphenylsilyl group, and a trisubstitued silyl group such as a trimethylsilyl group, a triethylsilyl group, a tri-n-propylsilyl group, a tri-isopropylsilyl group, a tri-n-butylsilyl group, a tri-sec-butylsilyl group, a tri-tert-butylsilyl group, a tri-isobutylsilyl group, a tert-butyldimethylsilyl group, a tri-n-pentylsilyl group, a tri-n-hexylsilyl group, a tricyclohexylsilyl group, and a triphenylsilyl group, preferably a trimethylsilyl group, a tert-butyldimethylsilyl group, and a triphenylsilyl group. Examples of the silyl group substituted with substituted C1-20 hydrocarbon include a silyl group substituted with a halogen (e.g. a fluorine atom)-substituted C1-20 hydrocarbon group.

Preferred transition metal complex of formula (1) is a transition metal complex wherein A and A' is a substituted or unsubstituted C6-18 phenylene group, and is represented by formula (2):

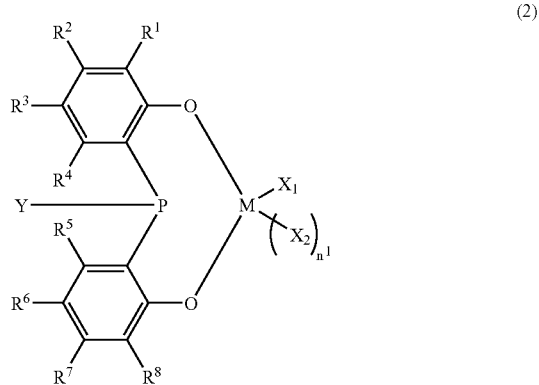

wherein M represents an element of Group 6 of Periodic Table of Elements, Y represents a substituted or unsubstituted C1-10 alkyl group, a substituted or unsubstituted C7-20 aralkyl group, a substituted or unsubstituted C6-20 aryl group, a silyl group substituted with a substituted or unsubstituted C1-20 hydrocarbon, $R^1$, $R^2$, $R^3$, $R^4$, $R^5$, $R^6$, $R^7$ and $R^8$ are the same or different, and represent a hydrogen atom, a halogen atom, an C1-10 alkyl group, an C1-10 alkoxy group, or a silyl group substituted with a C1-20 hydrocarbon, $X^1$ and $X^2$ are the same or different, and represent a hydrogen atom, a halogen atom, a substituted or unsubstituted C1-10 alkyl group, a substituted or unsubstituted C7-20 aralkyl group, a substituted or unsubstituted C6-20 aryl group, a substituted or unsubstituted C1-10 alkoxy group, a substituted or unsubstituted C7-20 aralkyloxy group, a substituted or unsubstituted C6-20 aryloxy group, or an amino group disubstituted with C1-20 hydrocarbon, and $n^1$ is an integer of 0 to 3.

In the transition metal complex of formula (2), examples of the halogen atom in $R^1$ to $R^8$ include a fluorine atom, a chlorine atom, a bromine atom, and an iodine atom, and preferred is a chlorine atom.

Examples of the unsubstituted C1-10 alkyl group in $R^1$ to $R^8$ include a methyl group, an ethyl group, a n-propyl group, an isopropyl group, a n-butyl group, a sec-butyl group, a tert-butyl group, a n-pentyl group, a neopentyl group, an amyl group, a n-hexyl group, a n-octyl group, a n-nonyl group, and a n-decyl group, and an C1-10 alkyl group substituted with a substituent selected from the group consisting of a halogen atom (preferably a fluorine atom, or a chlorine atom etc.), an alkoxy group (e.g. a methoxy group, an ethoxy group etc.), an aryloxy group (e.g. a phenoxy group etc.), an amino group substituted with hydrocarbon (e.g. a dimethylamino group etc.) and a silyl group substituted with hydrocarbon (e.g. a trimethylsilyl group etc.), and specific examples thereof include a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorodecyl group, a trichloromethyl group, a methoxymethyl group, a phenoxymethyl group, a dimethylaminomethyl group, and a trimethylsilylmethyl group. Among them, a methyl group, an ethyl group, an isopropyl group, a tert-butyl group and an amyl group are preferred, and a tert-butyl group is more preferred.

In $R^1$ to $R^8$, examples of the unsubstituted C1-10 alkoxy group include a methoxy group, a n-ethoxy group, a n-propoxy group, an isopropoxy group, a n-butoxy group, a sec-butoxy group, a tert-butoxy group, a n-pentyloxy group, a neopentyloxy group, a n-hexyloxy group, a n-octyloxy group, a n-nonyloxy group, and n-decyloxy group. Examples of the substituted C1-10 alkoxy group include an C1-10 alkoxy group substituted with a halogen atom (e.g. a fluorine atom or a chlorine atom etc.), an alkoxy group (e.g. a methoxy group, an ethoxy group etc.), an aryloxy group (e.g. a phenoxy group etc.), an amino group substituted with hydrocarbon (e.g. a dimethylamino group etc.), or a silyl group substituted with hydrocarbon (e.g. a trimethylsilyl group etc.).

Examples of the substituted alkoxy group include a fluoromethoxy group, a difluoromethoxy group, a trifluoromethoxy group, a fluoroethoxy group, a difluoroethoxy group, a trifluoroethoxy group, a tetrafluoroethoxy group, a pentafluoroexhoxy group, a perfluoropropoxy group, a perfluorobutyloxy group, a perfluoropentyloxy group, a perfluorohexyloxy group, a perfluorooctyloxy group, a perfluorodecyloxy group, a trichloromethoxy group, a methoxymethoxy group, a phenoxymethoxy group, a dimethylaminomethoxy group, and a trimethylsilylmethoxy group. Preferred alkoxy groups are a methoxy group, an ethoxy group, and a tert-butoxy group.

In $R^1$ to $R^8$, examples of the hydrocarbon group of the silyl group substituted with unsubstituted C1-20 hydrocarbon include an C1-10 alkyl group such as a methyl group, an ethyl group, an-propyl group, an isopropyl group, an-butyl group, a sec-butyl group, a tert-butyl group, a n-pentyl group, a neopentyl group, an amyl group, a n-hexyl group, a cyclohexyl group, a n-octyl group, or a n-decyl group, and an C6-20 aryl group such as a phenyl group, a tolyl group, a xylyl group, a naphtyl group, or an anthracenyl group.

Examples of the silyl group substituted with the C1-20 hydrocarbon include a monosubstituted silyl group such as a methylsilyl group, an ethylsilyl group, or a phenylsilyl group, a disubstitued silyl group such as a dimethylsilyl group, a diethylsilyl group, or a diphenylsilyl group, and a trisubstituted silyl group such as a trimethylsilyl group, a triethylsilyl group, a tri-n-propylsilyl group, a tri-isopropylsilyl group, a tri-n-butylsilyl group, a tri-sec-butylsilyl group, a tri-tert-butylsilyl group, a tri-isobutylsilyl group, a tert-butyldimethylsilyl group, a tri-n-pentylsilyl group, a tri-n-hexylsilyl group, a tricyclohexylsilyl group, or a triphenylsilyl group, preferred is a trimethylsilyl group, a tert-butyldimethylsilyl group, or a triphenylmethyl group. Examples of the substituted hydrocarbon group of the silyl group substituted with substituted C1-20 hydrocarbon include such groups wherein the hydrocarbon group is substituted with a halogen atom, for example, a fluorine atom.

Y of the compound of formula (1), (2) or (3) represents a substituted or unsubstituted C1-10 alkyl group, a substituted or unsubstituted C7-20 aralkyl group, a substituted or unsubstituted C6-20 aryl group, or a silyl group substituted with substituted or unsubstituted C1-20 hydrocarbon.

In Y, examples of the unsubstituted C1-10 alkyl group include a methyl group, an ethyl group, a n-propyl group, an isopropyl group, an-butyl group, a sec-butyl group, a tert-butyl group, a n-pentyl group, a neopentyl group, an amyl group, a n-hexyl group, a n-octyl group, or a n-decyl group, examples of the substituted C1-10 alkyl group include an C1-10 alkyl group substituted with an alkoxy group (e.g. a methoxy group etc.), or aryloxy group (e.g. a phenoxy group), and specific examples thereof include a methoxymethyl group, and a phenoxymethyl group. Among them, a methyl group, an ethyl group, an isopropyl group, and a tert-butyl group are preferred, and a tert-butyl group is more preferred.

In Y, examples of the unsubstituted C7-20 aralkyl group include a benzyl group, a naphthylmethyl group, an anthracenylmethyl group, a diphenylmethyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, and a (n-dodecylphenyl)methyl group, and examples of the substituted C7-20 aralkyl group include an C7-20 aralkyl group substituted with a group selected from an alkoxy group (e.g. a methoxy group etc.) and an aryloxy group (e. g. a phenoxy group etc.), and specific examples thereof include a (methoxyphenyl)methyl group, and a (phenoxyphenyl)methyl group. Preferred aralkyl group is a benzyl group.

In Y, examples of the unsubstituted C6-20 aryl group include a phenyl group, a naphthyl group, an anthracenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, and a n-tetradecylphenyl group. Examples of the substituted C6-20 aryl group include an C6-20 aryl group substituted with an alkoxy group (e.g. a methoxy group etc.) or an aryloxy group (e.g. a phenoxy group etc.), and specific examples thereof include a 2-methoxyphenyl group, a 3-methoxyphenyl group, a 4-methoxyphenyl group, and a 4-phenoxyphenyl group. Preferred aryl group is a phenyl group.

Examples of the hydrocarbon group of the silyl group substituted with a unsubstituted C1-20 hydrocarbon represented by Y include an C1-10 alkyl group such as a methyl group, an ethyl group, an-propyl group, a isopropyl group, an-butyl group, a sec-butyl group, a tert-butyl group, a n-pentyl group, a neopentyl group, an amyl group, a n-hexyl group, a cyclohexyl group, a n-octyl group, or a n-decyl group, and an C6-20 aryl group such as a phenyl group, a tolyl group, a xylyl group, a naphthyl group, or an anthracenyl group. Examples of the silyl group substituted with the C1-20 hydrocarbon include a monosubstituted silyl group such as a methylsilyl group, an ethylsilyl group, or a phenylsilyl group, a disubstituted silyl group such as a dimethylsilyl group, a diethylsilyl group, or a diphenylsilyl group, and a trisubstituted silyl group such as a trimethylsilyl group, a triethylsilyl group, a tri-n-propylsilyl group, a tri-isopropylsilyl group, a tri-n-butylsilyl group, a tri-sec-butylsilyl group, a tri-tert-butylsilyl group, a tri-isobutylsilyl group, a tert-butyldimethyl silyl group, a tri-n-pentylsilyl group, a tri-n-hexylsilyl group, a tricyclohexylsilyl group, or a triphenylsilyl group, examples of the hydrocarbon group of the silyl group substituted with substituted C1-20 hydrocarbon include a C1-20 hydrocarbon group substituted with a substituent selected from an alkoxy group or an aryloxy group, and preferred are a trimethylsilyl group, a tert-butyldimethylsilyl group, and a triphenylsilyl group.

M of the compound of formula (1), (2) or (4) represents an element of Group 6 of Periodic Table of Elements, specifically, a chromium atom, a molybdenum atom, and a tungsten atom, preferred is a chromium atom.

Examples of the unsubstituted C1-10 alkyl group represented by $X^1$, $X^2$, $X^3$, $X^4$ and $X^5$ in the compound of formula (1), (2) or (4) include a methyl group, an ethyl group, an-propyl group, an isopropyl group, a n-butyl group, a sec-butyl group, a tert-butyl group, a n-pentyl group, a neopentyl group, an amyl group, a n-hexyl group, a n-octyl group, and a n-decyl group. Examples of the substituted C1-10 alkyl group include an C1-10 alkyl group substituted with a substituent selected from the group consisting of a halogen atom (e.g. a fluorine atom or a chlorine atom etc.), an alkoxyl group (e.g. a methoxy group etc.), an aryloxy group (e.g. a phenoxy group etc.), an amino group substituted with hydrocarbon (e.g. a dimethylamino group etc.), and a silyl group substituted with hydrocarbon (e.g. a trimethylsilyl group etc.), and specific examples thereof include a fluoromethyl group, a difluoromethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluoroethyl group, a perfluorooctyl group, a perfluorodecyl group, a trichloromethyl group, a methoxymethyl group, a phenoxymethyl group, a dimethylaminomethyl group, and a trimethylsilylmethyl group. Among them, preferred are a methyl group, an ethyl group, an isopropyl group, a tert-butyl group, and an amyl group, and more preferred is a methyl group.

Examples of the unsubstituted C7-20 aralkyl group in $X^1$ to $X^5$ in the compound of the formula (1), (2) or (4) include a benzyl group, a naphthylmethyl group, an anthracenylmethyl group, a diphenylmethyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethtylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylpentyl)methyl group, a (n-butylphenyl)methyl group, a (sec-butylphenyl)methyl group, a (tert-butylheptyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, and a (n-dodecylphenyl)methyl group. Examples of the substituted C7-20 aralkyl group include an C7-20 aralkyl group substituted with a halogen atom (e.g. a fluorine atom or a chlorine atom etc.), an alkoxy group (e.g. a methoxy group etc.), an aryloxy group (e.g. a phenoxy group etc.), an amino group substituted with hydrocarbon (e.g. a dimethylamino group etc.), or a silyl group substituted with hydrocarbon (e.g. a trimethylsilyl group etc.), and specific examples thereof include a (fluorophenyl)methyl group, a (difluorophenyl)methyl group, a (pentafluorophenyl)methyl group, a (chlorophenyl)methyl group, a (methoxyphenyl)methyl group, a (phenoxyphenyl)methyl group, a (dimethylaminophenyl)methyl group, and a (trimethylsilylphenyl)methyl group. Preferred aralkyl group is a benzyl group.

Examples of the unsubstituted C6-20 aryl group in $X^1$ to $X^5$ in the compound of formula (1), (2) or (4) include a phenyl group, a naphthyl group, an anthracenyl group, 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, and a n-tetradecylphenyl group. Examples of the substituted C6-20 aryl group include an C6-20 aryl group substituted with a substituent selected from the group consisting of a halogen atom (e.g. a fluorine atom etc.), an alkoxy group (e.g. a methoxy group etc.), an aryloxy group (e.g. a phenoxy group etc.), an amino group substituted with hydrocarbon (e.g. a dimethylamino group etc.), and a silyl group substituted with hydrocarbon (e.g. a trimethylsilyl group etc.), and specific examples thereof include a 2-fluorophenyl group, a 3-fluorophenyl group, a 4-fluorophenyl group, a 3,5-difluorophenyl group, a pentafluorophenyl group, a 4-chlrophenyl group, a 2-methoxyphenyl group, a 3-methoxyphenyl group, a 4-methoxyphenyl group, a 4-phenoxyphenyl group, a 4-dimethylaminophenyl group, and a 4-trimethylsilylphenyl group. Preferred aryl group is a phenyl group.

Examples of the unsubstituted C1-10 alkoxyl group in $X^1$ to $X^5$ in the compound of formula (1), (2) or (4) include a methoxy group, an ethoxy group, a n-propoxy group, an isopropoxy group, a n-butoxy group, a sec-butoxy group, a tert-butoxy group, a n-pentyloxy group, a neopentyloxy group, a n-hexyloxy group, a n-octyloxy group, a n-nonyloxy group, and a n-decyloxy group. Examples of the substituted C1-10 alkoxyl group include an alkoxyl group substituted with a substituent selected from the group consisting of a halogen atom (e.g. a fluorine atom or a chlorine atom etc.), an alkoxy group (e.g. a methoxy group etc.), an aryloxy group (e.g. a phenoxy group etc.), an amino group substituted with hydrocarbon (e.g. a dimethylamino group etc.), and a silyl group substituted with hydrocarbon (e.g. a trimethylsilyl group etc.), and specific examples thereof include a fluoromethoxy group, a difluoromethoxy group, a trifluoromethoxy group, a fluoroethoxy group, a difluoroethoxy group, a trifluoroethoxy group, a tetrafluoroethoxy group, a pentafluoroethoxy group, a perfluoropropoxy group, a perfluorobutyloxy group, a perfluoropentyloxy group, a perfluorohexyloxy group, a perfluorooctyloxy group, a perfluorodecyloxy group, a trichloromethoxy group, a methoxymethoxy group, a phenoxymethoxy group, a dimethylaminomethoxy group, and a trimethylsilylmethoxy group. Preferred substituted or unsubstituted C1-10 alkoxyl group are a methoxy group, an ethoxy group, and a tert-butoxy group.

Examples of the unsubstituted C7-20 aralkyloxy group in $X^1$ to $X^5$ in the compound of formula (1), (2) or (4) include a benzyloxy group, a naphtylmethoxy group, an anthracenylmethoxy group, a diphenylmethoxy group, a (2-methylphenyl)methoxy group, a (3-methyophenyl)methoxy group, a (4-methylphenyl)methoxy group, a (2,3-dimethylphenyl)methoxy group, a (2,4-dimethylpehnyl)methoxy group, a (2,5-dimethylphenyl)methoxy group, a (2,6-dimethylphenyl)methoxy group, a (3,4-dimethylphenyl)methoxy group, a (2,3,4-trimethylphenyl)methoxy group, a (2,3,5-trimethylphenyl)methoxy group, a (2,3,6-trimethylphenyl)methoxy group, a (3,4,5-trimethylphenyl)methoxy group, a (2,4,6-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-pentylphenyl)methoxy group, a (neopentylphenyl)methoxy group, a (n-hexylphenyl)methoxy group, a (n-octylphenyl)methoxy group, a (n-decylphenyl)methoxy group, and a (n-dodecylphenyl)methoxy group. Examples of the substituted C7-20 aralkyloxy group include the aralkyloxy group substituted with a substituent selected from the group consisting of a halogen atom (e.g. a chlorine atom or a fluorine atom etc.), an alkoxy group (e.g. a methoxy group etc.), an aryloxy group (e.g. a phenoxy group etc.), an amino group substituted with hydrocarbon (e.g. a dimethylamino group etc.) and a silyl group substituted with hydrocarbon (e.g. a trimethylsilyl group etc.), and specific examples thereof include a (fluorophenyl)methyl group, a (difluorophenyl) methyl group, a (pentafluorophenyl)methyl group, a (chlorophenyl)methyl group, a (methoxyphenyl)methyl group, a (phenoxyphenyl)methyl group, a (dimethylaminophenyl)methyl group, and a (trimethylsilylphenyl)methyl group. Preferred aralkyloxy group is a benzyloxy group.

Examples of the unsubstituted C6-20 aryloxy group in $X^1$ to $X^5$ in the compound of formula (1), (2) or (4) include a phenoxy group, a naphthoxy group, an anthracenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, and a n-tetradecylphenoxy group. Examples of the substituted C6-20 aryloxy group include an aryloxy group substituted with a substituent selected from the group consisting of a halogen atom (e.g. a chlorine atom or a fluorine atom etc.), an alkoxy group (e.g. a methoxy group etc.), an aryloxy group (a phenoxy group etc.), an amino group substituted with hydrocarbon (e. g. a dimethylamino group etc.), and a silyl group substituted with hydrocarbon (e.g. a trimethylsilyl group etc.), and specific examples thereof include a 2-fluorophenoxy group, a 3-fluorophenoxy group, a 4-fluorophenoxy group, a 3,5-difluorophenoxy group, a pentafluorophenoxy group, a 2-methoxyphenoxy group, a 4-chlorophenoxy group, a 2-methoxyphenoxy group, a 3-methoxyphenoxy group, a 4-methoxyphenoxy group, a 4-phenoxyphenoxy group, a 4-dimethylaminophenoxy group, and a 4-trimethylsilylphenoxy group. Preferred substituted or unsubstituted C7-20 aryloxy group is a phenoxy group.

Examples of the hydrocarbon group in an amino group disubstituted with C1-20 hydrocarbon in $X^1$ to $X^5$ in the compound of formula (1), (2) or (4) include an C1-10 alkyl group such as a methyl group, an ethyl group, a n-propyl group, an isopropyl group, a n-butyl group, a sec-butyl group, a tert-butyl group, a n-pentyl group, a neopentyl group, an amyl group, a n-hexyl group, a cyclohexyl group, a n-octyl group, or a n-decyl group, and an C6-20 aryl group such as a phenyl group, a tolyl group a xylyl group, a naphthyl group, or an anthracenyl group. Examples of the amino group substituted with C1-20 hydrocarbon include a dimethylamino group, a diethylamino group, a di-n-propylamino group, a diisopropylamino group, a di-n-butylamino group, a di-sec-butylamino group, a di-tert-butylamino group, a di-isobutylamino group, a tert-butylisopropylamino group, a di-n-hexylamino group, a di-n-octylamino group, a di-n-decylamino group, and a diphenylamino group, and preferred is a dimethylamino group, or a diethylamino group.

Examples of the halogen atom in $X^1$ to $X^5$ in the compound of formula (1), (2) or (4) include a fluorine atom, a chlorine atom, a bromine atom, and an iodine atom, and preferred is a chlorine atom.

Examples of the neutral ligand represented by $L_0$ include a molecule having a neutral functional group such as ether, sulfide, amine, phosphine and olefin, and a neutral ligand may have a plurality of coordinating functional groups in its molecule.

Examples of the neutral ligand include dimethyl ether, diethyl ether, methyl tert-butyl ether, furan, tetrahydrofuran, dimethoxyethane, diethoxyethane, dimethyl sulfide, diethyl sulfide, methyl tert-butyl sulfide, thiophene, tetrahydrothiophene, ethylenedithiol dimethyl sulfide, ethylenedithiol diethyl sulfide, trimethylamine, triethylamine, triphenylamine, tricyclohexylamine, pyridine, 2,2'-bipyridine, tetramethylethylenediamine, tetraethylethylenediamine, triphenylphosphine, tricyclohexylphosphine, tri-tert-butylphosphine, bis(diphenylphosphino)methane, bis(diphenylphosphino)ethane, bis(diphenylphosphino)propane, bis(diphenylphosphino)binaphthyl, ethylene, propylene, butene, butadiene, octene, octadiene, cyclohexene, cyclohexadiene, norbornene, and norbornadiene.

Examples of the transition metal complex of formula (1) include 2,2'-(phenylphosphido)bisphenoxychromium chloride, 2,2'-(phenylphosphido)bis(4-methylphenoxy)chromium chloride, 2,2'-(phenylphosphido)bis(4,6-dimethylphenoxy)chromium chloride, 2,2'-(phenylphosphido)bis(4-tert-butyl-6-methylphenoxy)chromium chloride, 2,2'-(phenylphosphido)bis(6-tert-butyl-4-methylphenoxy) chromium chloride, 2,2'-(phenylphosphido)bis(4,6-di-tert-butylphenoxy)chromium chloride, 2,2'-(phenylphosphido) bis(4-methoxyphenoxy)chromium chloride, 2,2'-(phenylphosphido)bis(6-bromophenoxy)chromium chloride, 2,2'-(phenylphosphido)bis(6-trimethylsilylphenoxy)chromium chloride, 2,2'-(methylphosphido)bisphenoxychromium chloride, 2,2'-(methylphosphido)bis(4-methylphenoxy)chromium chloride, 2,2'-(methylphosphido)bis(4,6-dimethylphenoxy) chromium chloride, 2,2'-(methylphosphido)bis(4-tert-butyl-6-methylphenoxy)chromium chloride, 2,2'-(methylphosphido)bis(6-tert-butyl-4-methylphenoxy)chromium chloride, 2,2'-(methylphosphido)bis(4,6-di-tert-butylphenoxy)chromium chloride, 2,2'-(methylphosphido)bis(4-methoxyphenoxy)chromium chloride, 2,2'-(methylphosphido)bis(6-bromophenoxy)chromium chloride, 2,2'-(methylphosphido)bis(6-trimethylsilylphenoxy)chromium chloride, 2,2'-(tert-butylphosphido)bisphenoxychromium chloride, 2,2'-(tert-butylphosphido)bis(4-methylphenoxy)chromium chloride, 2,2'-(tert-butylphosphido)bis(4,6-dimethylphenoxy)chromium chloride, 2,2'-(tert-butylphosphido)bis(4-tert-butyl-6-methylphenoxy)-chromium chloride, 2,2'-(tert-butylphosphido)bis(6-tert-butyl-4-methylphenoxy) chromium chloride, 2,2'-(tert-butylphosphido)bis(4,6-di-tert-butylphenoxy)-chromium chloride, 2,2'-(tert-butylphosphido)bis(4-methoxyphenoxy)chromium chloride, 2,2'-(tert-butylphosphido)bis(6-bromophenoxy)chromium chloride, 2,2'-(tert-butylphosphido)bis(6-trimethylsilylphenoxy)chromium chloride, 2,2'-(cyclohexylphosphido)bisphenoxychromium chloride, 2,2'-(cyclohexylphosphido)bis(4-methylphenoxy)chromium chloride, 2,2'-(cyclohexylphosphido)bis(4,6-dimethylphenoxy)chromium chloride, 2,2'-(cyclohexylphosphido) bis(4-tert-butyl-6-methylphenoxy)chromium chloride, 2,2'-(cyclohexylphosphido)bis(6-tert-butyl-4-methylphenoxy) chromium chloride, 2,2'-(cyclohexylphosphido)bis(4,6-di-tert-butylphenoxy)chromium chloride, 2,2'-(cyclohexylphosphido)bis(4-methoxyphenoxy)chromium chloride, 2,2'-(cyclohexylphosphido)bis(6-bromophenoxy) chromium chloride, 2,2'-(cyclohexylphosphido)bis(6-trimethylsilylphenoxy)-chromium chloride, 2,2'-(benzylphosphido)bisphenoxychromium chloride, 2,2'-(benzylphosphido)bis(4-methylphenoxy)chromium chloride, 2,2'-(benzylphosphido)bis(4,6-dimethylphenoxy) chromium chloride, 2,2'-(benzylphosphido)bis(4-tert-butyl- 6-methylphenoxy)chromium chloride, 2,2'-(benzylphosphido)bis(6-tert-butyl-4-methylphenoxy)chromium chloride, 2,2'-(benzylphosphido)bis(4,6-di-tert-butylphenoxy)chromium chloride, 2,2'-(benzylphosphido)bis(4-methoxyphenoxy)chromium chloride, 2,2'-(benzylphosphido)bis(6-bromophenoxy)chromium chloride, 2,2'-(benzylphosphido)bis(6-trimethylsilylphenoxy)chromium chloride, 2,2'-(trimethylsilylphosphido)bisphenoxychromium chloride, 2,2'-(trimethylsilylphosphido)bis(4-methylphenoxy) chromium chloride, 2,2'-(trimethylsilylphosphido)bis(4,6-dimethylphenoxy)-chromium chloride, 2,2'-(trimethylsilylphosphido)bis(4-tert-butyl-6-methyl-phenoxy)chromium chloride, 2,2'-(trimethylsilylphosphido) bis(6-tert-butyl-4-methyl-phenoxy)chromium chloride, 2,2'-(trimethylsilylphosphido)bis(4,6-di-tert-butylphenoxy) chromium chloride, 2,2'-(trimethylsilylphosphido)bis(4-methoxyphenoxy)chromium chloride, 2,2'-(trimethylsilylphosphido)bis(6-bromophenoxy)chromium chloride, and 2,2'-(trimethylsilylphosphido)bis(6-trimethylsilylphenoxy)chromium chloride, and compounds in which the chromium is replaced by molybdenum or tungsten, and compounds in which chloride is replaced by bromide, iodide, methoxide, isopropoxide, butoxide, dimethylamide, ethylamide, methyl, or trimethylsilylmethyl.

The compound of formula (3) can be prepared according to the method described in JP-A No. 9-104691.

Examples of the compound of formula (3) include: bis(hydroxymethyl)methylphosphine, bis(hydroxymethyl)isopropylphosphine, bis(hydroxymethyl)ethylphosphine, bis(hydroxymethyl)-n-propylphosphine, bis(hydroxymethyl)-n-butylphosphine, bis(hydroxymethyl)-t-butylphosphine, bis(hydroxymethyl)benzylphosphine, bis(hydroxymethyl)phenylphosphine, bis(hydroxymethyl)mesitylphosphine, bis(hydroxymethyl)(3-chrorophenyl)phosphine, bis(hydroxymethyl)(trimethylsilyl)phosphine, bis(hydroxymethyl)(diphenylmethylsilyl)phosphine, bis(hydroxymethyl)(dimethylphenylsilyl)phosphine, bis(2-hydroxyethyl)methylphosphine, bis(2-hydroxyethyl)isopropylphosphine, bis(2-hydroxyethyl)ethylphosphine, bis(2-hydroxyethyl)-n-propylphosphine, bis(2-hydroxyethyl)-n-butylphosphine, bis(2-hydroxyethyl)-t-butylphosphine, bis(2-hydroxyethyl)benzylphosphine, bis(2-hydroxyethyl)phenylphosphine, bis(2-hydroxyethyl)mesitylphosphine, bis(2-hydroxyethyl)(3-chlorophenyl)phosphine, bis(2-hydroxyethyl)(trimethylsilyl)phosphine, bis(2-hydroxyethyl)(diphenylmethylsilyl)phosphine, bis(2-hydroxyethyl)(dimethylphenylsilyl)phosphine, bis(3-hydroxypropyl)methylphosphine, bis(3-hydroxypropyl)isopropylphosphine, bis(3-hydroxypropyl)ethylphosphine, bis(3-hydroxypropyl)-n-propylphosphine, bis(3-hydroxypropyl)-n-butylphosphine, bis(3-hydroxypropyl)-tert-butylphosphine, bis(3-hydroxypropyl)benzylphosphine, bis(3-hydroxypropyl)phenylphosphine, bis(3-hydroxypropyl)mesitylphosphine, bis(3-hydroxypropyl)(3-chlorophenyl)phosphine, bis(3-hydroxypropyl)(trimethylsilyl)phosphine, bis(3-hydroxypropyl)(diphenylmethylsilyl)phosphine, bis(3-hydroxypropyl)(dimethylphenylsilyl)phosphine, bis(1-hydroxyethyl)methylphosphine, bis(1-hydroxyethyl)isopropylphosphine, bis(1-hydroxyethyl)ethylphosphine, bis(1-hydroxyethyl)-n-propylphosphine, bis(1-hydroxyethyl)-n-butylphosphine, bis(1-hydroxyethyl)-tert-butylphosphine, bis(1-hydroxyethyl)benzylphosphine, bis(1-hydroxyethyl)phenylphosphine, bis(1-hydroxyethyl)mesitylphosphine, bis(1-hydroxyethyl)(3-chlorophenyl)phosphine, bis(1-hydroxyethyl)(trimethylsilyl)phosphine, bis(1-hydroxyethyl)(diphenylmethylsilyl)phosphine, bis(1-hydroxyethyl)(dimethylphenylsilyl)phosphine, bis(2-hydroxyethylenyl)methylphosphine, bis(2-hydroxyethylenyl)isopropylphosphine, bis(2-hydroxyethylenyl)ethylphosphine, bis(2-hydroxyethylenyl)-n-propylphosphine, bis(2-hydroxyethylenyl)-n-butylphosphine, bis(2-hydroxyethylenyl)-tert-butylphosphine, bis(2-hydroxyethylenyl)benzylphosphine, bis(2-hydroxyethylenyl)phenylphosphine, bis(2-hydroxyethylenyl)mesitylphosphine, bis(2-hydroxyethylenyl)(3-chlorophenyl)phosphine, bis(2-hydroxyethylenyl)(trimethylsilyl)phosphine, bis(2-hydroxyethylenyl)(diphenylmethylsilyl)phosphine, bis(2-hydroxyethylenyl)(dimethylphenylsilyl)phosphine, bis(3-hydroxypropenyl)methylphosphine, bis(3-hydroxypropenyl)isopropylphosphine, bis(3-hydroxypropenyl)ethylphosphine, bis(3-hydroxypropenyl)-n-propylphosphine, bis(3-hydroxypropenyl)-n-butylphosphine, bis(3-hydroxypropenyl)-tert-butylphosphine, bis(3-hydroxypropenyl)benzylphosphine, bis(3-hydroxypropenyl)phenylphosphine, bis(3-hydroxypropenyl)mesitylphosphine, bis(3-hydroxypropenyl)(3-chlorophenyl)phosphine, bis(3-hydroxypropenyl)(trimethylsilyl)phosphine, bis(3-hydroxypropenyl)(diphenylmethylsilyl)phosphine, bis(3-hydroxypropenyl)(dimethylphenylsilyl)phosphine, bis(2-hydroxyphenyl)methylphosphine, bis(2-hydroxyphenyl)isopropylphosphine, bis(2-hydroxyphenyl)ethylphosphine, bis(2-hydroxyphenyl)-n-propylphosphine, bis(2-hydroxyphenyl)-n-butylphosphine, bis(2-hydroxyphenyl)-tert-butylphosphine, bis(2-hydroxyphenyl)benzylphosphine, bis(2-hydroxyphenyl)phenylphosphine, bis(2-hydroxyphenyl)mesitylphosphine, bis(2-hydroxyphenyl)-(3-chlorophenyl)phosphine, bis(2-hydroxyphenyl)-(trimethylsilyl)phosphine, bis(2-hydroxyphenyl)-(diphenylmethylsilyl)phosphine, bis(2-hydroxyphenyl)-(dimethylphenylsilyl)phosphine, bis(2-hydroxy-3-methylphenyl)methylphosphine, bis(2-hydroxy-3-methylphenyl)isopropylphosphine, bis(2-hydroxy-3-methylphenyl)ethylphosphine, bis(2-hydroxy-3-methylphenyl)-n-propylphosphine, bis(2-hydroxy-3-methylphenyl)-n-butylphosphine, bis(2-hydroxy-3-methylphenyl)-tert-butylphosphine, bis(2-hydroxy-3-methylphenyl)benzylphosphine, bis(2-hydroxy-3-methylphenyl)phenylphosphine, bis(2-hydroxy-3-methylphenyl)mesitylphosphine, bis(2-hydroxy-3-methylphenyl)(3-chlorophenyl)phosphine, bis(2-hydroxy-3-methylphenyl)(trimethylsilyl)phosphine, bis(2-hydroxy-3-methylphenyl)(diphenylmethylsilyl)phosphine, bis(2-hydroxy-3-methylphenyl)(dimethylphenylsilyl)phosphine bis(2-hydroxy-5-methylphenyl)methylphosphine, bis(2-hydroxy-5-methylphenyl)isopropylphosphine, bis(2-hydroxy-5-methylphenyl)ethylphosphine, bis(2-hydroxy-5-methylphenyl)-n-propylphosphine, bis(2-hydroxy-5-methylphenyl)-n-butylphosphine, bis(2-hydroxy-5-methylphenyl)-t-butylphosphine, bis(2-hydroxy-5-methylphenyl)benzylphosphine, bis(2-hydroxy-5-methylphenyl)phenylphosphine, bis(2-hydroxy-5-methylphenyl)mesitylphosphine, bis(2-hydroxy-5-methylphenyl)(3-chlorophenyl)phosphine, bis(2-hydroxy-5-methylphenyl)(trimethylsilyl)phosphine, bis(2-hydroxy-5-methylphenyl)(diphenylmethylsilyl)phosphine, bis(2-hydroxy-5-methylphenyl)(dimethylphenylsilyl)phosphine bis(2-hydroxy-3-tert-butylphenyl)methylphosphine, bis(2-hydroxy-3-t-butylphenyl)isopropylphosphine, bis(2-hydroxy-3-t-butylphenyl)ethylphosphine, bis(2-hydroxy-3-t-butylphenyl)-n-propylphosphine, bis(2-hydroxy-3-t-butylphenyl)-n-butylphosphine, bis(2-hydroxy-3-t- butylphenyl)-t-butylphosphine, bis(2-hydroxy-3-t-butylphenyl)benzylphosphine, bis(2-hydroxy-3-t-butylphenyl)phenylphosphine, bis(2-hydroxy-3-t-butylphenyl)mesitylphosphine, bis(2-hydroxy-3-t-butylphenyl)(3-chlorophenyl)phosphine, bis(2-hydroxy-3-t-butylphenyl)(trimethylsilyl)phosphine, bis(2-hydroxy-3-t-butylphenyl)(diphenylmethylsilyl)phosphine, bis(2-hydroxy-3-t-butylphenyl)(dimethylphenylsilyl)phosphine, bis(2-hydroxy-5-tert-butylphenyl)methylphosphine, bis(2-hydroxy-5-t-butylphenyl)isopropylphosphine, bis(2-hydroxy-5-tert-butylphenyl)ethylphosphine, bis(2-hydroxy-5-tert-butylphenyl)-n-propylphosphine, bis(2-hydroxy-5-tert-butylphenyl)-n-butylphosphine, bis(2-hydroxy-5-tert-butylphenyl)-tert-butylphosphine, bis(2-hydroxy-5-tert-butylphenyl)benzylphosphine, bis(2-hydroxy-5-tert-butylphenyl)phenylphosphine, bis(2-hydroxy-5-tert-butylphenyl)mesitylphosphine, bis(2-hydroxy-5-tert-butylphenyl)(3-chlorophenyl)phosphine, bis(2-hydroxy-5-tert-butylphenyl)(trimethylsilyl)phosphine, bis(2-hydroxy-5-tert-butylphenyl)(diphenylmethylsilyl)phosphine, bis(2-hydroxy-5-tert-butylphenyl)(dimethylphenylsilyl)phosphine, bis(2-hydroxy-3-butyl-5-methylphenyl)methylphosphine, bis(2-hydroxy-3-butyl-5-methylphenyl)isopropylphosphine, bis(2-hydroxy-3-butyl-5-methylphenyl)ethylphosphine, bis(2-hydroxy-3-butyl-5-methylphenyl)-n-propylphosphine, bis(2-hydroxy-3-butyl-5-methylphenyl)-n-butylphosphine, bis(2-hydroxy-3-butyl-5-methylphenyl)-tert-butylphosphine, bis(2-hydroxy-3-butyl-5-methylphenyl)benzylphosphine, bis(2-hydroxy-3-butyl-5-methylphenyl)phenylphosphine, bis(2-hydroxy-3-butyl-5-methylphenyl)mesitylphosphine, bis(2-hydroxy-3-butyl-5-methylphenyl)(3-chlorophenyl)phosphine, bis(2-hydroxy-3-butyl-5-methylphenyl)(trimethylsilyl)phosphine, bis(2-hydroxy-3-butyl-5-methylphenyl)(diphenylmethylsilyl)phosphine, bis(2-hydroxy-3-butyl-5-methylphenyl)(dimethylphenylsilyl)-phosphine, bis(2-hydroxy-5-butyl-3-methylphenyl)methylphosphine, bis(2-hydroxy-5-butyl-3-methylphenyl)isopropylphosphine, bis(2-hydroxy-5-butyl-3-methylphenyl)ethylphosphine, bis(2-hydroxy-5-butyl-3-methylphenyl)-n-propylphosphine, bis(2-hydroxy-5-butyl-3-methylphenyl)-n-butylphosphine, bis(2-hydroxy-5-butyl-3-methylphenyl)-tert-butylphosphine, bis(2-hydroxy-5-butyl-3-methylphenyl)benzylphosphine, bis(2-hydroxy-5-butyl-3-methylphenyl)phenylphosphine, bis(2-hydroxy-5-butyl-3-methylphenyl)mesitylphosphine, bis(2-hydroxy-5-butyl-3-methylphenyl)(3-chlorophenyl)phosphine, bis(2-hydroxy-5-butyl-3-methylphenyl)(trimethylsilyl)phosphine, bis(2-hydroxy-5-butyl-3-methylphenyl)(diphenylmethylsilyl)phosphine, bis(2-hydroxy-5-butyl-3-methylphenyl)(dimethylphenylsilyl)phosphine, bis(2-hydroxy-3,5-dimethylphenyl)methylphosphine, bis(2-hydroxy-3,5-dimethylphenyl)isopropylphosphine, bis(2-hydroxy-3,5-dimethylphenyl)ethylphosphine, bis(2-hydroxy-3,5-dimethylphenyl)-n-propylphosphine, bis(2-hydroxy-3,5-dimethylphenyl)-n-butylphosphine, bis(2-hydroxy-3,5-dimethylphenyl)-tert-butylphosphine, bis(2-hydroxy-3,5-dimethylphenyl)benzylphosphine, bis(2-hydroxy-3,5-dimethylbenyl)phenylphosphine, bis(2-hydroxy-3,5-dimethylphenyl)mesitylphosphine, bis(2-hydroxy-3,5-dimethylphenyl)(3-chlorophenyl)phosphine, bis(2-hydroxy-3,5-dimethylphenyl)(trimethylsilyl)phosphine, bis(2-hydroxy-3,5-dimethylphenyl)(diphenylmethylsilyl)phosphine, bis(2-hydroxy-3,5-dimethylphenyl)(dimethylphenylsilyl)phosphine, bis(2-hydroxy-3,5-dibutylphenyl)methylphosphine, bis(2-hydroxy-3,5-dibutylphenyl)isopropylphosphine, bis(2-hydroxy-3,5-dibutylphenyl)ethylphosphine, bis(2-hydroxy-3,5-dibutylphenyl)-n-propylphosphine, bis(2-hydroxy-3,5-dibutylphenyl)-n-butylphosphine, bis(2-hydroxy-3,5-dibutylphenyl)-tert-butylphosphine, bis(2-hydroxy-3,5-dibutylphenyl)benzylphosphine, bis(2-hydroxy-3,5-dibutylphenyl)phenylphosphine, bis(2-hydroxy-3,5-dibutylphenyl)mesitylphosphine, bis(2-hydroxy-3,5-dibutylphenyl)(3-chlorophenyl)phosphine, bis(2-hydroxy-3,5-dibutylphenyl)(trimethylsilyl)phosphine, bis(2-hydroxy-3,5-dibutylphenyl)(diphenylmethylsilyl)phosphine, bis(2-hydroxy-3,5-dibutylphenyl)(dimethylphenylsilyl)phosphine, bis(2-hydroxy-3-methyl-5-methoxyphenyl)methylphosphine, bis(2-hydroxy-3-methyl-5-methoxyphenyl)isopropylphosphine, bis(2-hydroxy-3-methyl-5-methoxyphenyl)ethylphosphine, bis(2-hydroxy-3-methyl-5-methoxyphenyl)-n-propylphosphine, bis(2-hydroxy-3-methyl-5-methoxyphenyl)-n-butylphosphine, bis(2-hydroxy-3-methyl-5-methoxyphenyl)-tert-butylphosphine, bis(2-hydroxy-3-methyl-5-methoxyphenyl)benzylphosphine, bis(2-hydroxy-3-methyl-5-methoxyphenyl)phenylphosphine, bis(2-hydroxy-3-methyl-5-methoxyphenyl)mesitylphosphine, bis(2-hydroxy-3-methyl-5-methoxyphenyl)(3-chlorophenyl)phosphine, bis(2-hydroxy-3-methyl-5-methoxyphenyl)(trimethylsilyl)phosphine, bis(2-hydroxy-3-methyl-5-methoxyphenyl)(diphenylmethylsilyl)phosphine, bis(2-hydroxy-3-methyl-5-methoxyphenyl)(dimethylphenylsilyl)phosphine, bis(2-hydroxy-3-trimethylsilylphenyl)methylphosphine, bis(2-hydroxy-3-trimethylsilylphenyl)isopropylphosphine, bis(2-hydroxy-3-trimethylsilylphenyl)ethylphosphine, bis(2-hydroxy-3-trimethylsilylphenyl)-n-propylphosphine, bis(2-hydroxy-3-trimethylsilylphenyl)-n-butylphosphine, bis(2-hydroxy-3-trimethylsilylphenyl)-tert-butylphosphine, bis(2-hydroxy-3-trimethylsilylphenyl)benzylphosphine, bis(2-hydroxy-3-trimethylsilylphenyl)phenylphosphine, bis(2-hydroxy-3-trimethylsilylphenyl)mesitylphosphine, bis(2-hydroxy-3-trimethylsilylphenyl)(3-chlorophenyl)phosphine, bis(2-hydroxy-3-trimethylsilylphenyl)(trimethylsilyl)phosphine, bis(2-hydroxy-3-trimethylsilylphenyl)(diphenylmethylsilyl)phosphine, bis(2-hydroxy-3-trimethylsilylphenyl)(dimethylphenylsilyl)phosphine, bis(2-hydroxy-3,5-dibromophenyl)methylphosphine, bis(2-hydroxy-3,5-dibromophenyl)isopropylphosphine, bis(2-hydroxy-3,5-dibromophenyl)ethylphosphine, bis(2-hydroxy-3,5-dibromophenyl)-n-propylphosphine, bis(2-hydroxy-3,5-dibromophenyl)-n-butylphosphine, bis(2-hydroxy-3,5-dibromophenyl)-tert-butylphosphine, bis(2-hydroxy-3,5-dibromophenyl)benzylphosphine, bis(2-hydroxy-3,5-dibromophenyl)phenylphosphine, bis(2-hydroxy-3,5-dibromophenyl)mesitylphosphine, bis(2-hydroxy-3,5-dibromophenyl)(3-chlorophenyl)phosphine, bis(2-hydroxy-3,5-dibromophenyl)(trimethylsilyl)phosphine, bis(2-hydroxy-3,5-dibromophenyl)(diphenylmethylsilyl)phosphine, bis(2-hydroxy-3,5-dibromophenyl)(dimethylphenylsilyl)phosphine, bis(2-hydroxy-1-naphthyl)methylphosphine, bis(2-hydroxy-1-naphthyl)isopropylphosphine, bis(2-hydroxy-1-naphthyl)ethylphosphine, bis(2-hydroxy-1-naphthyl)-n-propylphosphine, bis(2-hydroxy-1-naphthyl)-n-butylphosphine, bis(2-hydroxy-1-naphthyl)-tert-butylphosphine, bis(2-hydroxy-1-naphthyl)benzylphosphine, bis(2-hydroxy-1-naphthyl)phenylphosphine, bis(2-hydroxy-1-naphthyl)

mesitylphosphine, bis(2-hydroxy-1-naphthyl)(3-chlorophenyl)phosphine, bis(2-hydroxy-1-naphthyl)(trimethylsilyl)phosphine, bis(2-hydroxy-1-naphthyl)(diphenylmethylsilyl)phosphine, bis(2-hydroxy-1-naphthyl)(dimethylphenylsilyl)phosphine, bis(1-hydroxy-2-naphthyl)methylphosphine, bis(1-hydroxy-2-naphthyl)isopropylphosphine, bis(1-hydroxy-2-naphthyl)ethylphosphine, bis(1-hydroxy-2-naphthyl)-n-propylphosphine, bis(1-hydroxy-2-naphthyl)-n-butylphosphine, bis(1-hydroxy-2-naphthyl)-tert-butylphosphine, bis(1-hydroxy-2-naphthyl)benzylphosphine, bis(1-hydroxy-2-naphthyl)phenylphosphine, bis(1-hydroxy-2-naphthyl)mesitylphosphine, bis(1-hydroxy-2-naphthyl)(3-chlorophenyl)phosphine, bis(1-hydroxy-2-naphthyl)(trimethylsilyl)phosphine, bis(1-hydroxy-2-naphthyl)(diphenylmethylsilyl)phosphine, bis(1-hydroxy-2-naphthyl)(dimethylphenylsilyl)phosphine, bis(dimethylsilanol)methylphosphine, bis(dimethylsilanol)isopropylphosphine, bis(dimethylsilanol)ethylphosphine, bis(dimethylsilanol)-n-propylphosphine, bis(dimethylsilanol)-n-butylphosphine, bis(dimethylsilanol)-tert-butylphosphine, bis(dimethylsilanol)benzylphosphine, bis(dimethylsilanol)phenylphosphine, bis(dimethylsilanol)mesitylphosphine, bis(dimethylsilanol)(3-chlorophenyl)phosphine, bis(dimethylsilanol)(trimethylsilyl)phosphine, bis(dimethylsilanol)(diphenylmethylsilyl)phosphine, bis(dimethylsilanol)(dimethylphenylsilyl)phosphine, bis(methylphenylsilanol)methylphosphine, bis(methylphenylsilanol)isopropylphosphine, bis(methylphenylsilanol)ethylphosphine, bis(methylphenylsilanol)-n-propylphosphine, bis(methylphenylsilanol)-n-butylphosphine, bis(methylphenylsilanol)-tert-butylphosphine, bis(methylphenylsilanol)benzylphosphine, bis(methylphenylsilanol)phenylphosphine, bis(methylphenylsilanol)mesitylphosphine, bis(methylphenylsilanol)(3-chlorophenyl)phosphine, bis(methylphenylsilanol)(trimethylsilyl)phosphine, bis(methylphenylsilanol)(diphenylmethylsilyl)phosphine, bis(methylphenylsilanol)(dimethylphenylsilyl)phosphine, bis(diphenylsilanol)methylphosphine, bis(diphenylsilanol)isopropylphosphine, bis(diphenylsilanol)ethylphosphine, bis(diphenylsilanol)-n-propylphosphine, bis(diphenylsilanol)-n-butylphosphine, bis(diphenylsilanol)-tert-butylphosphine, bis(diphenylsilanol)benzylphosphine, bis(diphenylsilanol)phenylphosphine, bis(diphenylsilanol)mesitylphosphine, bis(diphenylsilanol)(3-chlorophenyl)phosphine, bis(diphenylsilanol)(trimethylsilyl)phosphine, bis(diphenylsilanol)(diphenylmethylsilyl)phosphine, bis(diphenylsilanol)(dimethylphenylsilyl)phosphine.

In addition, examples of the transition metal compound of formula (4) include trichlorochromium, trichlorochromium-3tetrahydrofuran complex, tris(bis[trimethylsilyl]methyl)chromium, dimesitylchromium tetrahydrofuran complex, dimesitylchromium 3tetrahydrofuran complex, trimesitylchromium tetrahydrofuran complex, chromium (II) acetylacetonate, bis(trifluoroacetoxy)chromium, tris(trifluoroacetoxy)chromium, trichloromolybdenum, pentachloromolybdenum, molybdenum acetate, triallylchloromolybdenum, mesitylenetricarbonylmolybdenum, tetracarbonyl[(1,2,5,6)-1,5-cyclooctadiene]molybdenum, tungsten tetrachloride, tungsten hexachloride, mesitylene tungsten tricarbonyl, tetrabenzyltungsten, tetramethyltungsten, pentamethyltungsten, benzyltetrachlorotungsten, phenyltrichlorotungsten, trimethylchlorotungsten, and tris(bis[trimethylsilyl]methyl)tungsten.

The transition metal complex of formula (1) can be obtained, for example, by reacting the compound of formula (3) with the transition metal compound of formula (4).

A mol ratio of the compound of formula (3) and the transition metal compound of formula (4) is not particularly limited, but is preferably in a range of 1:0.1 to 1:10, more preferably a range of 1:0.5 to 1:2.

Upon a reaction, a base is used, if necessary. Examples of the base include, for example, an organic alkali metal compound such as an organic lithium compound such as methyllithium, ethyllithium, n-butyllithium, sec-butyllithium, tert-butyllithium, lithiumtrimethylsilylacetylide, lithiumacetylide, trimethylsilylmethyllithium, vinyllithium, phenyllithium and allyllithium, and the amount of the base is usually in a range of 0.5 to 5 moles per mol of the compound of formula (3).

The aforementioned reaction is usually performed in a solvent which is inert to a reaction. Examples of such the solvent include an aprotic solvent such as an aromatic hydrocarbon solvent such as benzene and toluene, an aliphatic hydrocarbon solvent such as hexane and heptane, an ether solvent such as diethyl ether, tetrahydrofuran, and 1,4-dioxane, an amide solvent such as hexamethylphosphoric amide, and dimethylformamide, a polar solvent such as acetonitrile, propionitrile, acetone, diethyl ketone, methyl isobutyl ketone, and cyclohexanone, and a halogenated solvent such as dichloromethane, dichloroethane, chlorobenzene, and dichlorobenzene. The solvents are used alone, or may be used by mixing two or more kinds. The amount of the solvent is usually in a range of 1 to 200 parts by weight, preferably 3 to 50 parts by weight per part by weight of the compound of formula (2).

An order of the aforementioned reaction is not particularly limited, but the reaction can be usually performed by adding a base to a solvent and the compound of formula (3), if necessary, and adding the transition metal compound of formula (4).

The reaction temperature is usually not lower than −100° C. to a boiling point of a solvent, preferably in a range of about −80 to 100° C.

The transition metal complex of formula (1) can be obtained from the resulting reaction mixture by a conventional method, for example, by a procedure of filtering produced precipitates, and concentrating the filtrate to precipitate a solid matter.

The transition metal complex of formula (1) obtained by the reaction of the compound of formula (3) with the transition metal compound of formula (4) may be used in the polymerization without purifying from a reaction solution.

The thus prepared transition metal complex of formula (1) can be used by charging a compound (A) or further a compound (B) in an optional order in polymerization, or a reaction product obtained by contacting a combination of those optional compounds before-hand may be used.

[Compound A]

As the compound (A) used in the present invention, the known organic aluminum compound can be used. Preferred compound (A) is any one of compounds ($A_1$) to ($A_3$), or a mixture of two or more of them.

Examples of the organic aluminum compound ($A_1$) of formula: $(E_1)_aAl(Z')_{(3-a)}$ include trialkylaluminum such as trimethylaluminum, triethylaluminum, tripropylaluminum, triisobutylaluminum, and trihexylaluminum; dialkylaluminum chloride such as dimethylaluminum chloride, diethylaluminum chloride, dipropylaluminum chloride, diisobutylaluminum chloride, and dihexylaluminum chloride;

alkylaluminum dichloride such as methylaluminum dichloride, ethylaluminum dichloride, propylaluminum dichloride, isobutylaluminum dichlofirde, hexylaluminum dichloride; dialkylaluminumhydride such as dimethylaluminum hydride, diethylaluminum hydride, dipropylaluminum hydride, diisobutylaluminum hydride, and dihexylaluminum hydride. Preferred is trialkylaluminum, and more preferred is triethylaluminum, or triisobutylaluminum.

Examples of $E_2$ or $E_3$ in cyclic aluminoxane ($A_2$) having a structure of formula: $\{-Al(E_2)-O-\}_b$ or linear aluminoxane ($A_3$) having a structure of formula: $(E_3)\{-Al(E_3)-O-\}_c Al(E_3)_2$ include an alkyl group such as a methyl group, an ethyl group, a normal propyl group, an isopropyl group, a normal butyl group, an isobutyl group, a normal pentyl group, and a neopentyl group. And, b is an integer of 2 or more, and c is an integer of 1 or more. Preferred $E_2$ and $E_3$ are a methyl group and an isobutyl group, b is 2 to 40, and c is around 1 to 40.

The aforementioned aluminoxane is prepared by various processes. The process is not particularly limited, but the aluminoxane may be prepared according to the known process. For example, the aluminoxane is prepared by contacting water with a solution in which trialkylaluminum (e.g. trimethylaluminum etc.) is dissolved in a suitable organic solvent (benzene, aliphatic hydrocarbon etc.). Alternatively, there can be exemplified a method of preparing the aluminoxane by contacting trialkylaluminum (e.g. trimethylaluminum) with a metal salt (e.g. copper sulfate hydrate etc.) containing crystal water.

Examples of the compound (B) used in the present invention include any one of boron compounds represented by ($B_1$), ($B_2$) or ($B_3$), or a mixture of two or more of them.

In the boron compound ($B_1$) of formula: $BQ_1Q_2Q_3$, B is a trivalent boron atom, and $Q_1$ to $Q_3$ are a halogen atom, a C1-20 hydrocarbon group, a halogenated C1-20 hydrocarbon group, a silyl group substituted with C1-20 hydrocarbon, an C1-20 alkoxy group, or an amino group disubstituted with C1-20 hydrocarbon, and may be the same or different. Preferred $Q_1$ to $Q_3$ are a halogen atom, a C1-20 hydrocarbon group, and a halogenated C1-20 hydrocarbon group.

Examples of ($B_1$) include tris(pentafluorophenyl)borane, tris(2,3,5,6-tetrafluorophenyl)borane, tris(2,3,4,5-tetrafuluorophenyl)borane, tris(3,4,5-trifluorophenyl)borane, tris(2,3,4-trifluorophenyl)borane, and phenylbis(pentafluorophenyl)borane, and preferred is tris(pentafluorophenyl)borane.

In the boron compound ($B_2$) of formula: $Z^+(BQ_1Q_2Q_3Q_4)^-$, $Z^+$ is an inorganic or organic cation, B is a trivalent boron atom, and examples of $Q_1$ to $Q_4$ include the same compound as those of $Q_1$ to $Q_3$.

In the compound of formula: $Z^+(BQ_1Q_2Q_3Q_4)^-$, examples of $Z^+$ which is an inorganic cation include a ferrocenium cation, an alkyl-substituted ferrocenium cation, and a silver cation, and examples of $Z^+$ which is an organic cation include a triphenylmethyl cation. Examples of $(BQ_1Q_2Q_3Q_4)^-$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate, and tetrakis(3,5-bistrifluoromethylphenyl)borate.

Examples of the compound of formula: $Z^+(BQ_1Q_2Q_3Q_4)^-$ include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, and triphenylmethyl tetrakis (3,5-bistrifluoromethylphenyl)borate, and preferred is triphenylmethyl tetrakis(pentafluorophenyl)borate.

In addition, in the boron compound ($B_3$) of formula: $(L-H)^+(BQ_1Q_2Q_3Q_4)^-$, L is a neutral Lewis base, $(L-H)^+$ is a Brönsted acid, B is a trivalent boron atom, and examples of $Q_1$ to $Q_4$ include the same compounds as those of $Q_1$ to $Q_3$ in ($B_1$).

In the compound of formula: $(L-H)^+(BQ_1Q_2Q_3Q_4)^-$, examples of $(L-H)^+$ which is a Brösted acid include trialkyl-substituted ammonium, N,N-dialkylanilinium, dialkylammonium, and triarylphosphonium, and examples of $(BQ_1Q_2Q_3Q_4)^-$ include the same ions as those described above.

Examples of the compound of formula: $(L-H)^+(BQ_1Q_2Q_3Q_4)^-$ include triethylammonium tetrakis(pentafluorophenyl)borate, tripropylammonium tetrakis(pentafluorophenyl)borate, tri(normal butyl)ammonium tetrakis (pentafluorophenyl)borate, tri(normal butyl)ammonium tetrakis(3,5-bistrifluoromethyphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluoro)borate, triphenylphosphonium tetrakis(pentafluorophenyl)borate, tri(methylphenyl)phosphonium tetrakis(pentafluorophenyl)borate, tri(dimethylphenyl)phosphonium tetrakis(pentafluorophenyl)borate, preferably tri(normal butyl)ammonium tetrakis(pentafluorophenyl)borate, and N,N-dimethylanilinium tetrakis(pentafluorophenyl)borate.

The amount of each catalyst component is suitably set so that a molar ratio of compound (A)/transition metal complex (1) is usually in a range of 0.1 to 10000, preferably 5 to 2000, and a molar ratio of compound (B)/transition metal complex (1) is usually in a range of 0.01 to 100, preferably 0.5 to 10.

Regarding the concentration when each catalyst component is used in a solution state, it is desirable to use each component so that the concentration of the transition metal complex (1) is usually in a range of 0.0001 to 5 mmol/liter, preferably in a range of 0.001 to 1 mmol/liter, and that of the compound (A) is usually in a range of 0.01 to 500 mmol/liter, preferably in a range of 0.1 to 100 mmol/liter in terms of an Al atom, and that of the component (B) is in a range of 0.0001 to 5 mmol/liter, preferably in a range of 0.001 to 1 mmol/liter.

In the present invention, as a monomer used for polymerization, any of olefin and diolefin having 2 to 20 carbon atoms can be used, and two or more kinds of monomers may be used at the same time. The monomer will be exemplified below, but the present invention is not limited to the following compounds. Examples of the olefin include ethylene, propylene, butene-1, pentene-1, hexene-1, heptene-1, octene-1, nonene-1, decene-1,5-methyl-2-pentene-1, and vinylcyclohexane.

Examples of the diolefin compound include a conjugated diene and non-conjugated diene hydrocarbon compounds and, specific examples of the compound include the non-conjugated diene compound such as 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, 5-methyl-2-norbornene, norbornadiene, 5-methylene-2-norbornene, 1,5-cyclooctadiene, or 5,8-endomethylenehexahydronaphthalene, and the conjugated diene compound such as 1,3-butadiene, isoprene, 1,3-hexadiene, 1,3-octadiene, 1,3-cyclooctadiene, or 1,3-cyclohexadiene.

Examples of the monomers constituting a copolymer include a combination of ethylene and propylene, ethylene and butene-1, ethylene and hexene-1, and propylene and butene-1, and a combination using further 5-ethylidene-2-norbornene in the combinations above, but the present invention is not limited to the above compounds.

In the present invention, as a monomer, an aromatic vinyl compound may be used. Examples of an aromatic vinyl compound include styrene, o-methylstyrene, m-methylstyrene, p-methylstyrene, o,p-dimethylstyrene, o-ethylstyrene, m-ethylstyrene, p-ethylstyrene, o-chlorostyrene, p-chlorostyrene, α-methylstyrene, and divinylbenzene.

The polymerization method is not particularly limited, but solvent polymerization or slurry polymerization using, as a solvent, an aliphatic hydrocarbon such as butane, pentane, hexane, heptane or octane, an aromatic hydrocarbon such as benzene or toluene, or halogenated hydrocarbon such as methylene dichloride, or vapor phase polymerization of a gaseous monomer is possible, and any of continuous polymerization and batch-type polymerization can be applied.

The polymerization temperature can be in a range of −50° C. to 200° C., in particular, preferably in a range of around −20° C. to 100° C., and a polymerization pressure is preferably normal pressure to 6 MPa (60 kg/cm² G). A polymerization time is generally selected appropriately depending on a kind of an objective polymer, and a reaction apparatus, and can be in a range of 1 minute to 20 hours. In addition, in the present invention, a chain transfer agent such as hydrogen may be added in order to regulate a molecular weight of a copolymer.

EXAMPLES

The present invention will be explained in more detail below by way of Examples, but the present invention is not limited to these Examples. Nature of polymers in Examples was measured by the following methods.

[Molecular Weight and Molecular Weight Distribution]

A molecular weight and a molecular weight distribution were measured under the following condition using Rapid-GPC.
Pumping apparatus: (LC pump) manufactured by Gilson, Inc., Model1305 (pump head 25.SC)
Column: manufactured by PolymerLaboratories (PL), PLgel Mixed-B 10 μm, 7.5 mmφ×300 mm
Mobile phase: o-dichlorobenzene
Dissolution solvent: 1,2,4-trichlorobenzene
Flow rate: 2 ml/min
Column temperature: 160° C.
Calibration line: PL standard polystyrene (PS) 8 samples, (standard PS molecular weight) 5,000, 10,050, 28,500, 65,500, 185,400, 483,000, 1,013,000, 3,390,000

[Melting Point]

A melting point was measured under the following condition using SAMMS (Sensor Array Modular System) (manufactured by Symyx Technologies, Inc.).
Measurement mode: Melting temperature measurement by heat capacity spectroscopy
Atmosphere gas: vacuum condition ($3.0 \times 10^{-4}$ Torr or less)
Temperature problem: (Start) room temperature, (Temperature raising rate) about 50° C./min, (Holding) 200° C.(0 min)

[Me Branching]

Me branching was measured under the following condition using IR (EQUINOX55 manufactured by Bruker).
Measurement mode: reflection transmission method (formation of film on mirror plane)
Blank: mirror plane (Air)
Measurement condition: (Resolution) 2 cm$^{-1}$, (Accumulated time) 128 times, (Wavelength) 400 to 4000 cm$^{-1}$ Synthesis Example Example 1

Synthesis of 2,2'-(phenylphosphido)bis(6-tert-butyl-4-methylphenoxy)chromium chloride To a solution (2.94 mL) of NaH (0.20 g, 5.00 mmol) in tetrahydrofuran was added dropwise a solution (3.91 mL) of bis(2-hydroxy-3-tert-butyl-5-methylphenyl)phenylphosphine (0.43 g, 1.00 mmol) in tetrahydrofuran at 0° C., and the mixture was stirred at room temperature for 3 hours. Excessive NaH was removed by filtration, and a solution (2.94 mL) of CrCl$_3$ (THF)$_3$ (0.37 g, 1.00 mmol) in tetrahydrofuran was added dropwise to the filtrate at 0° C. The mixture was stirred at room temperature for 10 hours, the solvent was distilled off under reduced pressure, toluene (10.0 mL) was added, insolubles were filtered off, and the filtrate was distilled off under reduced pressure to quantitatively obtain 2,2'-(phenylphosphido)bis(6-tert-butyl-4-methylphenoxy)chromium chloride as a green solid.
MS spectrum (EI) 519 (M$^+$)

Example 2

Synthesis of bis(2-methoxymethoxy-3-tert-butyl-5-methylphenyl)(tert-butyl)phosphine To a solution (28.1 mL) of 2-tert-butyl-1-methoxymethoxy-4-methylbenzene (4.17 g, 20 mmol) in tetrahydrofuran was added a 1.57 M solution (15.3 mL) of n-butyllithium in hexane at 0° C., and the temperature was raised to room temperature, followed by stirring for 1 hour. To the reaction mixture was added a solution (18.8 mL) of tert-butyldichlorophosphine (1.75 g, 11.0 mmol) in tetrahydrofuran at 0° C., and the mixture was stirred at room temperature for 15 hours. The solvent was distilled off under reduced pressure, toluene (20.0 mL) was added, insolubles were filtered off, and the filtrate was concentrated under reduced pressure to quantitatively obtain bis(2-methoxymethoxy-3-tert-butyl-5-methylphenyl)(tert-butyl)phosphine as a yellow liquid.
$^1$H NMR (C$_6$D$_6$) δ1.30(d, J=12.4 Hz, 9H), 1.51(18H), 2.12(6H), 3.52(6H), 5.46-5.72(4H), 7.16(2H), 7.30(2H)
$^{31}$P NMR (C$_6$D$_6$) δ−4.2

Example 3

Synthesis of bis(2-hydroxy-3-tert-butyl-5-methylphenyl)(tert-butyl)phosphine)

To an ethyl acetate/methanol=1/1 solution (60 mL) of bis(2-methoxymethoxy-3-tert-butyl-5-methylphenyl)(tert-butyl)phosphine (1.01 g, 2 mmol) was added acetyl chloride (0.79 g, 10.0 mmol) at room temperature, and the mixture was stirred at room temperature for 15 hours. The solvent was distilled off under reduced pressure to quantitatively obtain bis(2-hydroxy-3-tert-butyl-5-methylphenyl)(tert-butyl)phosphine as a pale yellow solid.

$^1$HNMR($C_6D_6$) δ 1.31(9H), 1.44(18H), 2.36(6H), 7.32 (2H) 7.49(2H) $^{31}$P NMR($C_6D_6$) δ–2.3

Example 4

Synthesis of 2,2'-(tert-butylphosphido)bis(6-tert-butyl-4-methylphenoxy)chromium chloride To a solution (2.70 mL) of NaH (0.18 g, 4.43 mmol) in tetrahydrofuran was added a solution (3.60 mL) of bis(2-hydroxy-3-tert-butyl-5-methylphenyl)(tert-butyl)phosphine (0.40 g, 0.89mmol) in tetrahydrofuran at 0° C., and the mixture was stirred at room temperature for 3 hours. Excessive NaH was removed by filtration, and a solution (2.70 mL) of $CrCl_3$ $(THF)_3$ (0.33 g, 0.89 mmol) in tetrahydrofuran was added dropwise to the filtrate at 0° C. The mixture was stirred at room temperature for 10 hours, the solvent was distilled off under reduced pressure, toluene (10.0 mL) was added, the insolubles were filtered off, and the filtrate was distilled off under reduced pressure to obtain 381.1 mg of 2,2'-(tert-butylphosphido)bis(2-tert-butyl-4-methylphenoxy)chromium chloride as a green solid.

MS spectrum (EI) 499 (M–1)

Example 5

Polymerization 5.0 mL of toluene was placed into a 23.5 mL autoclave under nitrogen, and stabilized at 40° C., and then ethylene was pressurized to 0.60 MPa therein and stabilized. Methylaluminoxane (100 μmol), and 2,2'-(phenylphosphido)bis(6-tert-butyl-4-methylphenoxy)chromium chloride (0.10 μmol) were added thereto to perform polymerization for 30 minutes. As a result of polymerization, $1.08 \times 10^7$ g of a polymer was prepared per 1 mol of chromium an hour.

Example 6

According to the same manner as that of Example 5 except that a solution of triisobutylaluminum in hexane (40 μL, 1.0 M, Kanto Kagaku) and pentafluorophenylborane (0.30 μmol) were used in place of methylaluminoxane, polymerization was performed. As a result of polymerization, $4.00 \times 10^6$ g of a polymer was prepared per 1 mol of chromium an hour.

Example 7

According to the same manner as that of Example 5 except that a solution of triisobutylaluminum in hexane (40 μL, 1.0 M, Kanto Kagaku) and dimethylanilinium tetrakis (pentafluorophenyl)borate (0.30 μmol) were used in place of methylaluminoxane, polymerization was performed. As a result of polymerization, $1.70 \times 10^7$ g of a polymer was prepared per 1 mol of chromium an hour.

Example 8

According to the same manner as that of Example 5 except that a solution of triisobutylaluminum in hexane (40 μL, 1.0 M, Kanto Kagaku) and triphenylmethyl tetrakis (pentafluorophenyl)borate (0.30 μmol) were used in place of methylaluminoxane, polymerization was performed. As a result of polymerization, $7.72 \times 10^7$ g of a polymer was prepared per 1 mol of chromium an hour.

Example 9

5.0 mL of toluene and 1-hexene (50 μL) were placed into a 23.5 mL autoclave under nitrogen, and stabilized at 40° C., and then ethylene was pressurized to 0.60 MPa therein and to stabilized. Methylaluminoxane (100 μmol), 2,2'-(phenylphosphido)bis(6-tert-butyl-4-methylphenoxy)chromium chloride (0.10 μmol) were added thereto, followed by polymerization for 30 minutes. As a result of polymerization, $1.11 \times 10^7$ g of a polymer having a molecular weight (Mw) $=2.33 \times 10^6$, a molecular weight distribution (Mw/Mn)=2.0, a melting point (Tm)=117.7° C., and Me branching of 9 per 1000 carbons was prepared per 1 mol of chromium an hour.

Example 10

According to the same manner as that of Example 9 except that a solution of triisobutylaluminum in hexane (40 μL, 1.0 M, Kanto Kagaku) and pentafluorophenylborane (0.30 μmol) were used in place of methylaluminoxane, polymerization was performed. As a result of polymerization, $7.40 \times 10^6$ g of a polymer having a molecular weight (Mw)=$1.19 \times 10^4$, a molecular weight distribution (Mw/Mn) =1.9, a melting point (Tm)=112.9° C., and Me branching of 8 per 1000 carbons was prepared per 1 mol of chromium an hour.

Example 11

According to the same manner as that of Example 9 except that a solution of triisobutylaluminum in hexane (40 μL, 1.0 M, Kanto Kagaku) and dimethylanilinium tetrakis (pentafluorophenyl)borate (0.30 μmol) were used in place of methylaluminoxane, polymerization was performed. As a result of polymerization, $4.72 \times 10^7$ g of a polymer having a molecular weight (Mw)=$9.74 \times 10^3$, a molecular weight distribution (Mw/Mn)=2.0, a melting point (Tm)=120.4° C., and Me branching of 14 per 1000 carbons was prepared per 1 mol of chromium an hour.

Example 12

According to the same manner as that of Example 9 except that a solution of triusobutylaluminum in hexane (40 μL, 1.0 M, Kanto Kagaku) and triphenylmethyl tetrakis (pentafluorophenyl)borate (0.30 μmol) were used in place of methylaluminoxane, polymerization was performed. As a result of polymerization, $5.82 \times 10^7$ g of a polymer having a molecular weight (Mw)=$2.71 \times 10^3$, a molecular weight distribution (Mw/Mn)=4.6, a melting point (Tm)=121.5° C. and Me branching of 17 per 1000 carbons was prepared per 1 mol of chromium an hour.

Example 13

5.0 mL of toluene and 1-hexene (50 μL) were placed into a 23.5 mL autoclave under nitrogen, and stabilized at 70° C., and then ethylene was pressurized to 0.60 MPa therein and stabilized. Pentafluorophenylborane (0.30 μmol) and 2,2'-(phenylphosphido)bis(6-tert-butyl-4-methylphenoxy)chromium chloride (0.10 μmol) were added thereto, followed by polymerization for 30 minutes. As a result of polymerization, $2.06 \times 10^7$ g of a polymer having a molecular weight (Mw)=$3.3 \times 10^3$, a molecular weight distribution (Mw/Mn)

=1.8, a melting point (Tm)=131° C., and Me branching of 4 per 1000 carbons was prepared per 1 mol of chromium an hour.

Example 14

5.0 mL of toluene was placed into a 23.5 mL autoclave under nitrogen, and stabilized at 40° C., and then ethylene was pressurized to 0.60 MPa therein and stabilized. Methylaluminoxane (100 μmol) was placed therein, and a toluene solution obtained by mixing bis(2-hydroxy-3-tert-butyl-5-methylphenyl)phenylphosphine (0.20 μmol) and $CrCl_3$ $(THF)_3$ (0.20 μmol) at 25° C. for 1 minute was added, and polymerization was carried out for 30 minutes. As a result of polymerization, $1.00 \times 10^5$ g of a polymer was prepared per 1 mol of chromium an hour.

Example 15

According to the same manner as that of Example 14 except that a solution of triisobutylaluminum in hexane (40 μL, 1.0 M, Kanto Kagaku) and pentafluorophenylborane (0.30 μmol) were used in place of methylaluminoxane, polymerization was performed. As a result of polymerization, $8.10 \times 10^6$ g of a polymer was prepared per 1 mol of chromium an hour.

Example 16

According to the same manner as that of Example 14 except that a solution of triisobutylaluminum in hexane (40 μL, 1.0 M, Kanto Kagaku) and dimethylanilinium tetrakis (pentafluorophenyl)borate (0.30 μmol) were used in place of methylaluminoxane, polymerization was performed. As a result of polymerization, $1.29 \times 10^7$ g of a polymer was prepared per 1 mol of chromium an hour.

Example 17

According to the same manner as that of Example 14 except that a solution of triisobutylaluminum in hexane (40 μL, 1.0 M, Kanto Kagaku) and triphenylmethyl tetrakis (pentafluorophenyl)borate (0.30 μmol) were used in place of methylaluminoxane, polymerization was performed. As a result of polymerization, $4.87 \times 10^7$ g of a polymer was prepared per 1 mol of chromium an hour.

Example 18

5.0 mL of toluene was placed into a 23.5 mL autoclave under nitrogen, and stabilized at 40° C., and then ethylene was pressurized to 0.60 MPa therein and stabilized. Methylaluminoxane (100 μmol) was placed therein, and a toluene solution obtained by mixing bis(2-hydroxy-3-tert-butyl-5-methylphenyl)phenylphosphine (0.40 μmol) and $CrCl_3$ $(THF)_3$ (0.20 μmol) at 25° C. for 1 minute was added, and polymerization was carried out for 30 minutes. As a result of polymerization, $1.00 \times 10^5$ g of a polymer was prepared per 1 mol of chromium an hour.

Example 19

According to the same manner as that of Example 18 except that a solution of triisobutylaluminum in hexane (40 μL, 1.0 M, Kanto Kagaku) and pentafluorophenylborane (0.30 μmol) were used in place of methylaluminoxane, polymerization was performed. As a result of polymerization, $9.80 \times 10^6$ g of a polymer was prepared per 1 mol of chromium an hour.

Example 20

According to the same manner as that of Example 18 except that a solution of triisobutylaluminum in hexane (40 μL, 1.0 M, Kanto Kagaku) and dimethylanilinium tetrakis (pentafluorophenyl)borate (0.30 μmol) were used in place of methylaluminoxane, polymerization was performed. As a result of polymerization, $1.41 \times 10^7$ g of a polymer was prepared per 1 mol of chromium an hour.

Example 21

According to the same manner as that of Example 18 except that a solution of triisobutylaluminum in hexane (40 μL, 1.0 M, Kanto Kagaku) and triphenylmethyl tetrakis (pentafluorophenyl)borate (0.30 μmol) were used in place of methylaluminoxane, polymerization was performed. As a result of polymerization, $7.98 \times 10^7$ g of a polymer was prepared per 1 mol of chromium an hour.

Example 22

5.0 mL of toluene was placed into a 23.5 mL autoclave under nitrogen, and stabilized at 40° C., and then ethylene was pressurized to 0.60 MPa therein and stabilized. Methylaluminoxane (100 μmol), and 2,2'-(tert-butylphosphido)bis (2-tert-butyl-4-methylphenoxy) chromium chloride (0.10 μmol) were added thereto, and polymerization was carried out for 30 minutes. As a result of polymerization, $1.33 \times 10^7$ g of a polymer was prepared per 1 mol of chromium an hour.

Example 23

According to the same manner as that of Example 22 except that a solution of triisobutylaluminum in hexane (40 μL, 1.0 M, Kanto Kagaku) and pentafluorophenylborane (0.30 μmol) were used in place of methylaluminoxane, polymerization was performed. As a result of polymerization, $1.00 \times 10^5$ g of a polymer was prepared per 1 mol of chromium an hour.

Example 24

According to the same manner as that of Example 22 except that a solution of triisobutylaluminum in hexane (40 μL, 1.0 M, Kanto Kagaku) and dimethylanilinium tetrakis (pentafluorophenyl)borate (0.30 μmol) were used in place of methylaluminoxane, polymerization was performed. As a result of polymerization, $2.12 \times 10^7$ g of a polymer was prepared per 1 mol of chromium an hour.

Example 25

According to the same manner as that of Example 22 except that a solution of triisobutylaluminum in hexane (40 μL, 1.0 M, Kanto Kagaku) and triphenylmethyl tetrakis (pentafluorophenyl)borate (0.30 μmol) were used in place of methylaluminoxane, polymerization was performed. As a result of polymerization, $1.65 \times 10^8$ g of a polymer was prepared per 1 mol of chromium an hour.

Example 26

5.0 mL of toluene and 1-hexene (50 µL) were placed into a 23.5 mL autoclave under nitrogen, and stabilized at 40° C., and then ethylene was pressurized to 0.60 MPa therein and stabilized. Methylaluminoxane (100 µmol) and 2,2'-(tert-butylphosphido)bis(6-tert-butyl-4-methylphenoxy)chromium chloride (0.10 µmol) were added thereto, and polymerization was carried out for 30 minutes. As a result of polymerization, $1.11 \times 10^7$ g of a polymer having a molecular weight (Mw)=$7.30 \times 10^3$, a molecular weight distribution (Mw/Mn)=2.0, a melting point (Tm)=114.5° C., and Me branching of 32 per 1000 carbons was prepared per 1 mol of chromium an hour.

Example 27

According to the same manner as that of Example 26 except that a solution of triisobutylaluminum in hexane (40 µL, 1.0 M, Kanto Kagaku) and pentafluorophenylborane (0.30 µmol) were used in place of methylaluminoxane, polymerization was performed. As a result of polymerization, $1.00 \times 10^5$ g of a polymer was prepared per 1 mol of chromium an hour.

Example 28

According to the same manner as that of Example 26 except that a solution of triisobutylaluminum in hexane (40 µL, 1.0 M, Kanto Kagaku) and dimethylanilinium tetrakis (pentafluorophenyl)borate (0.30 µmol) were used in place of methylaluminoxane, polymerization was performed. As a result of polymerization, $2.77 \times 10^7$ g of a polymer having a molecular weight (Mw)=$9.00 \times 10^3$, a molecular weight distribution (Mw/Mn)=1.7, a melting point (Tm)=117.7° C., and Me branching of 23 per 1000 carbons was prepared per 1 mol of chromium an hour.

Example 29

According to the same manner as that of Example 26 except that a solution of triisobutylaluminum in hexane (40 µL, 1.0 M, Kanto Kagaku) and triphenylmethyl tetrakis (pentafluorophenyl)borate (0.30 µmol) were used in place of methylaluminoxane, polymerization was performed. As a result of polymerization, $1.59 \times 10^8$ g of a polymer having a molecular weight (Mw)=$8.30 \times 10^3$, a molecular weight distribution (Mw/Mn)=1.7, a melting point (Tm)=116.6° C., and Me branching of 20 per 1000 carbons was prepared per 1 mol of chromium an hour.

Example 30

5.0 mL of toluene and 1-hexene (50 µL) were placed into a 23.5 mL autoclave under nitrogen, and stabilized at 70° C., and then ethylene was pressurized to 0.60 MPa therein and stabilized. Methylaluminoxane (100 µmol) and 2,2'-(tert-butylphosphido)bis(6-tert-butyl-4-methylphenoxy)chromium chloride (0.10 µmol) were added thereto, and polymerization was carried out for 30 minutes. As a result, $9.00 \times 10^5$ g of a polymer was prepared per 1 mol of chromium an hour.

Example 31

According to the same manner as that of Example 30 except that a solution of triisobutylaluminum in hexane (40 µL, 1.0 M, Kanto Kagaku) and dimethylanilinium tetrakis (pentafluorophenyl)borate (0.30 µmol) were used in place of methylaluminoxane, polymerization was performed. As a result of polymerization, $4.10 \times 10^6$ g of a polymer having a molecular weight (Mw)=$4.00 \times 10^3$, a molecular weight distribution (Mw/Mn)=1.5, a melting point (Tm)=122.1° C. and Me branching of 27 per 1000 carbons was prepared per 1 mol of chromium an hour.

Example 32

According to the same manner as that of Example 30 except that a solution of triisobutylaluminum in hexane (40 µL, 1.0 M, Kanto Kagaku) and triphenylmethyl tetrakis (pentafluorophenyl)borate (0.30 µmol) were used in place of methylaluminoxane, polymerization was performed. As a result of polymerization, $4.87 \times 10^7$ g of a polymer having a molecular weight (Mw)=$6.50 \times 10^3$, a molecular weight distribution (Mw/Mn)=1.53, a melting point (Tm)=123.10C., and Me branching of 15 per 1000 carbons was prepared per 1 mol of chromium an hour.

Example 33

5.0 mL of toluene and 1-hexene (50 µL) were placed into a 23.5 mL autoclave under nitrogen, and stabilized at 130° C., and then ethylene was pressurized to 0.60 Mpa therein and stabilized. Methylaluminoxane (100 µmol) and 2,2'-(tert-butylphosphido)bis(6-tert-butyl-4-methylphenoxy) chromium chloride (0.10 µmol) were added thereto, and polymerization was carried out for 30 minutes. As a result of polymerization, $5.00 \times 10^5$ g of a polymer was prepared per 1 mol of chromium an hour.

Example 34

According to the same manner as that of Example 33 except that a solution of triisobutylaluminum in hexane (40 µL, 1.0 M, Kanto Kagaku) and dimethylanilinium tetrakis (pentafluorophenyl)borate (0.30 µmol) were used in place of methylaluminoxane, polymerization was performed. As a result of polymerization, $3.00 \times 10^5$ g of a polymer was prepared per 1 mol of chromium an hour.

Example 35

According to the same manner as that of Example 33 except that a solution of triisobutylaluminum in hexane (40 µL, 1.0 M, Kanto Kagaku) and triphenylmethyl tetrakis (pentafluorophenyl)borate (0.30 µmol) were used in place of methylaluminoxane, polymerization was performed. As a result of polymerization, $6.00 \times 10^5$ g of a polymer was prepared per 1 mol of chromium an hour.

Comparative Example 1

5.0 mL of toluene was placed into a 23.5 mL autoclave under nitrogen, and stabilized at 40° C., and then ethylene was pressurized to 0.60 MPa therein and stabilized. A solution of triisobutylaluminum in hexane (40 µL, 1.0 M, Kanto Kagaku), triphenylmethyl tetrakis (pentafluorophenyl)borate (0.30 µmol) and 2,2'-(phenylphosphido)bis(6-tert-butyl-4-methylphenoxy)(tetrahydrofuran)titanium dichloride (0.10 µmol) were added thereto, and polymerization was carried out for 30 minutes. As a result of polymerization, $1.30 \times 10^6$ g of a polymer was prepared per 1 mol of titanium an hour.

Comparative Example 2

5.0 mL of toluene and 1-hexene (50 μL) were placed into a 23.5 mL autoclave under nitrogen, and stabilized at 40° C., and then ethylene was pressurized to 0.60MPa therein and stabilized. A solution of triisobutylaluminum in hexane (40 μL, 1.0 M, Kanto Kagaku), dimethylanilinium tetrakis(pentafluorophenyl)borate (0.30 μmol) and 2,2'-(phenylphosphido)bis(6-tert-butyl-4-methylphenoxy)(tetrahydrofuran) titanium dichloride (0.10 μmol) were added thereto, and polymerization was carried out for 30 minutes. As a result of polymerization, $7.00 \times 10^5$ g of a polymer was prepared per 1 mol of titanium an hour.

INDUSTRIAL APPLICABILITY

Using a transition metal complex obtained by the present invention as a catalytic component, polyolefin can be prepared with better catalyst activity.

The invention claimed is:

1. A transition metal complex of formula (2):

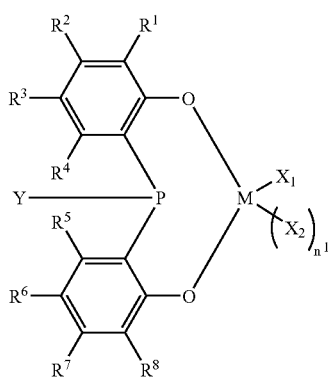

(2)

wherein M represents Cr,
Y represents a substituted or unsubstituted C1-10 alkyl group,
a substituted or unsubstituted C7-20 aralkyl group,
a substituted or unsubstituted C6-20 aryl group,
a silyl group substituted with substituted or unsubstituted C1-20 hydrocarbon,
$R^1$, $R^2$, $R^3$, $R^4$, $R^5$, $R^6$, $R^7$ and $R^8$ are the same or different and represent a hydrogen atom, a halogen atom, an C1-10 alkyl group, an C1-10 alkoxyl group, or a silyl group substituted with C1-20 hydrocarbon,
$X^1$ and $X^2$ are the same or different, and represent a hydrogen atom, a halogen atom,
a substituted or unsubstituted C1-10 alkyl group,
a substituted or unsubstituted C7-20 aralkyl group,
a substituted or unsubstituted C6-20 aryl group,
a substituted or unsubstituted C1-10 alkoxy group,
a substituted or unsubstituted C7-20 aralkyloxy group,
a substituted or unsubstituted C6-20 aryloxy group, or
an amino group disubstituted C1-20 hydrocarbon, and
$n^1$ is an integer of 0 to 3.

2. The transition metal complex according to claim 1 wherein Y is a substituted or unsubstituted C1-10 alkyl group, or a substituted or unsubstituted C6-20 aryl group.

3. An olefin polymerization catalyst obtained by combining the transition metal complex as defined in claim 1 or 2 with the following compound (A),
Compound (A): any one of the following compounds ($A_1$) to ($A_3$), or a mixture of two or more of them
($A_1$): an organic aluminum compound of formula $(E_1)_a Al(Z')_{(3-a)}$,
($A_2$): cyclic aluminoxane having a structure of formula $\{-Al(E_2)-O-\}_b$,
($A_3$): linear aluminoxane having a structure of formula $(E_3)\{-Al(E_3)-O-\}_c Al(E_3)_2$
wherein $B_1$ to $B_3$ are the same or different, and represent a C1-8 hydrocarbon group, Z's are the same or different, and represent a hydrogen atom or a halogen atom, a represents 1,2 or 3, b is an integer of 2 or more, and c represents an integer of 1 or more.

4. The olefin polymerization catalyst according to claim 3, which is obtained by further combining the following compound (B),
Compound (B): any one of the following compounds ($B_1$) to ($B_3$), or a mixture of two or more of them
($B_1$): a boron compound of formula $BQ_1Q_2Q_3$,
($B_2$): a boron compound of formula $Z^+(BQ_1Q_2Q_3Q_4)^-$,
($B_3$): a boron compound of formula $(L-H)^+ (BQ_1Q_2Q_3Q_4)^-$,
wherein B is a trivalent boron atom, $Q_1$ to $Q_4$ are the same or different and represent a halogen atom, a C1-20 hydrocarbon group, a halogenated C1-20 hydrocarbon group, a silyl group substituted with C1-20 hydrocarbon, an C1-20 alkoxy group, or an amino group disubstituted with C1-20 hydrocarbon, $Z^+$ represents an inorganic or organic cation, and L represents a neutral Lewis base.

5. A process for preparing an olefin polymer, which comprises polymerizing olefin by contacting an olefin with an olefin polymerization catalyst as defined in claim 3.

6. A process for preparing an olefin polymer, which comprises polymerizing olefin by contacting an olefin with the olefin polymerizing catalyst as defined in claim 4.

* * * * *